(12) United States Patent
Kim et al.

(10) Patent No.: US 8,855,753 B2
(45) Date of Patent: Oct. 7, 2014

(54) APPARATUS AND METHOD FOR MEASURING A BIOLOGICAL SIGNAL

(75) Inventors: Jong-pal Kim, Seoul (KR); Byung-hoon Ko, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 187 days.

(21) Appl. No.: 13/155,824

(22) Filed: Jun. 8, 2011

(65) Prior Publication Data

US 2011/0306892 A1    Dec. 15, 2011

(30) Foreign Application Priority Data

Jun. 10, 2010 (KR) .................. 10-2010-0055111

(51) Int. Cl.
*A61B 5/04* (2006.01)
*A61B 5/0408* (2006.01)
*A61B 5/0428* (2006.01)
*A61B 5/00* (2006.01)

(52) U.S. Cl.
CPC ............. *A61B 5/0408* (2013.01); *A61B 5/0428* (2013.01); *A61B 5/6843* (2013.01); *A61B 2562/0209* (2013.01); *A61B 2562/046* (2013.01); *A61B 2562/125* (2013.01); *Y10S 128/901* (2013.01)
USPC .......................................... 600/509; 128/901

(58) Field of Classification Search
USPC ......... 600/509, 309, 345, 300, 528, 547, 513; 128/901; 607/62
See application file for complete search history.

(56) References Cited

U.S. PATENT DOCUMENTS

| 4,112,930 | A | 9/1978 | Feldman et al. |
| 4,537,200 | A * | 8/1985 | Widrow ........................ 600/509 |
| 4,890,630 | A | 1/1990 | Kroll et al. |
| 5,704,365 | A | 1/1998 | Albrecht et al. |
| 6,073,039 | A | 6/2000 | Berson |
| 6,287,328 | B1 | 9/2001 | Snyder et al. |
| 7,711,414 | B2 * | 5/2010 | Shin et al. ..................... 600/509 |
| 2001/0051821 | A1 | 12/2001 | Snyder |
| 2003/0171661 | A1 * | 9/2003 | Tong ............................. 600/300 |
| 2008/0287767 | A1 | 11/2008 | Pasveer et al. |
| 2010/0036230 | A1 * | 2/2010 | Greene et al. ................. 600/391 |

FOREIGN PATENT DOCUMENTS

| JP | 2001-286450 | 10/2001 |
| KR | 10-2000-0038310 | 7/2000 |
| KR | 10-2005-0061756 | 6/2005 |
| KR | 10-2005-0072941 | 7/2005 |
| KR | 10-2006-0116190 | 11/2006 |
| KR | 10-2007-0014251 | 2/2007 |
| KR | 10-2007-0043124 | 4/2007 |
| KR | 10-0721803 | 4/2007 |

(Continued)

OTHER PUBLICATIONS

Extended European Search Report issued Oct. 6, 2011, in counterpart European Application No. 11169277.8, 8pp.

*Primary Examiner* — Catherine Voorhees
(74) *Attorney, Agent, or Firm* — NSIP Law (57) ABSTRACT

Provided is a method and apparatuses for measuring a biological signal, in which a biological signal of an examinee is detected via at least one interface that touches skin of the examinee, and a dummy signal is detected via a dummy interface Noise that is generated by a fluctuation in the electrical characteristics of the at least one interface is removed from the biological signal using the biological signal and the dummy signal.

9 Claims, 9 Drawing Sheets

(56) References Cited

FOREIGN PATENT DOCUMENTS

| KR | 10-0725580 A | 6/2007 |
| KR | 10-0825888 B1 | 4/2008 |
| KR | 10-2008-0059822 | 7/2008 |
| KR | 10-2008-0074413 | 8/2008 |
| KR | 10-2008-0097934 | 11/2008 |
| KR | 10-2009-0030122 | 3/2009 |
| WO | WO 2010/023615 A1 | 3/2010 |
| WO | WO 2011/007292 A1 | 1/2011 |

\* cited by examiner

APPARATUS AND METHOD FOR MEASURING A BIOLOGICAL SIGNAL

CROSS-REFERENCE TO RELATED APPLICATION(S)

This application claims the benefit under 35 U.S.C. §119(a) of Korean Patent Application No. 10-2010-0055111, filed on Jun. 10, 2010, in the Korean Intellectual Property Office, the entire disclosure of which is incorporated herein by reference for all purposes.

BACKGROUND

1. Field

The following description relates to methods and apparatuses for measuring a biological signal, and more particularly, to methods and apparatuses for accurately measuring a biological signal by removing noise from the biological signal.

2. Description of the Related Art

To examine a patient's health, various medical equipment has been used and more are currently being developed. Various medical equipment may be used to measure electrical biological signals of a patient such as electrocardiography signals, brain wave signals, electromyogram signals, and the like. Recently, equipment for measuring biological signals have gained more attention as they provide convenience for patients and examination results quickly.

However, various factors may create noise that affects the measurement of the biological signals. The noise may disrupt the biological signal and prevent an accurate reading from being detected.

SUMMARY

In one general aspect, there is provided a biological signal measuring apparatus including at least one interface for detecting a biological signal of an examinee through electrical interfacing with the skin of the examinee, at least one dummy interface for detecting a dummy signal that is different from the biological signal, through the at least one dummy interface that has electrical characteristics that are different from those of the at least one interface, a noise extracting unit for extracting a signal that is proportional to noise generated due to a fluctuation in the electrical characteristics of the at least one interface, from the biological signal and the dummy signal, and a biological signal extracting unit for removing the noise from the detected biological signal using the extracted signal.

The at least one interface and the at least one dummy interface may be placed within a predetermined distance from each other.

The at least one interface may comprise a plurality of unit electrodes that are arranged on a substrate, and the at least one dummy interface may comprise a plurality of unit dummy electrodes that are arranged between the unit electrodes in such a way that the at least one interface and the at least one dummy interface are placed near to each other.

The noise extracting unit may extract a signal that is proportional to the noise using a similarity between fluctuations in the electrical characteristics of the at least one interface and the at least one dummy interface, which is due to the at least one interface and the at least one dummy interface being placed near to each other.

An electrode of the at least one dummy interface may be formed of a material that is different from that of an electrode of the at least one interface so that the at least one dummy interface has electrical characteristics that are different from those of the at least one interface.

The at least one interface may comprise a first electrode and a second electrode, the at least one dummy interface comprises a first dummy electrode and a second dummy electrode, and the noise extracting unit extracts a signal that is proportional to the noise by measuring a voltage between the first electrode and the first dummy electrode, measuring a voltage between the second electrode and the second dummy electrode, and calculating a difference in the measured voltages.

The at least one dummy interface may have electrical characteristics that are different from those of the at least one interface because the at least one dummy interface may have formed therein an insulation layer that is located at a portion of the at least one dummy interface that touches the skin of the examinee to reduce current from flowing from the skin of the examinee to the at least one dummy interface.

The at least one interface may comprise a first electrode and a second electrode, the at least one dummy interface may comprise a first dummy electrode and a second dummy electrode, the noise extracting unit may extract a signal that is proportional to the noise by measuring a voltage between the first dummy electrode and the second dummy electrode, and potentials of voltage sources of the first dummy electrode and the second dummy electrode may be approximately the same.

The biological signal may be an electrocardiography signal of the examinee, and the noise may be a motion artifact that is generated by fluctuation in the electrical characteristics of the at least one interface due to an external factor caused by motion of the examinee.

In another aspect, there is provided a method of measuring a biological signal, the method including receiving a biological signal of an examinee from at least one interface that touches skin of the examinee, receiving a dummy signal that is different from the biological signal, from at least one dummy interface that has electrical characteristics that are different from those of the at least one interface, and removing noise generated by a fluctuation in the electrical characteristics of the at least one interface from the biological signal using the biological signal and the dummy signal.

The at least one interface and the at least one dummy interface may be placed within a predetermined distance from each other.

The removing of noise may comprise extracting a signal that is proportional to the noise generated by the fluctuation in the electrical characteristics of the at least one interface from the biological signal and the dummy signal, and removing the noise from the detected biological signal using the extracted signal.

In the extracting of the signal that is proportional to the noise, the signal that is proportional to the noise may be extracted using a similarity between fluctuations of the electrical characteristics of the at least one interface and the at least one dummy interface, which is due to the at least one interface and the at least one dummy interface being placed near to each other.

The biological signal may be an electrocardiography signal of the examinee, and the noise may be a motion artifact that is generated by a fluctuation in the electrical characteristics of the interface due to external factor caused by motion of the examinee.

In another aspect, there is provided a computer readable storage medium comprising program instructions to cause a processor to execute a method of measuring a biological signal, the method including receiving a biological signal of an examinee from at least one interface that touches skin of the examinee, receiving a dummy signal that is different from the biological signal, from at least one dummy interface that has electrical characteristics that are different from those of the at least one interface, and removing noise generated by a fluctuation in the electrical characteristics of the at least one interface from the biological signal using the biological signal and the dummy signal.

In another aspect, there is provided an interface device for detecting a biological signal of an examinee and a signal for removing noise of the biological signal, the interface including at least one interface for detecting a biological signal of the examinee through electrical interfacing with skin of the examinee, and at least one dummy interface for detecting a dummy signal that is different from the biological signal, through the at least one dummy interface that has electrical characteristics that are different from those of the at least one interface.

In another aspect, there is provided a device for extracting noise from a measured biological signal, the device including a noise extracting unit for extracting a noise signal from the measured biological signal based on the measured biological signal and a measured dummy biological signal, and a biological signal extracting unit for removing the noise from the detected biological signal using the extracted noise signal.

The noise signal may be generated by a fluctuation in electrical characteristics of an interface that measures the biological signal and an interface that measures the dummy signal.

The biological signal may be measured with a first interface and the dummy signal may be measured with a second interface, and the first interface and the second interface may have different electrical characteristics.

The first interface and the second interface may be within a predetermined distance from each other on an examinee's body.

The different electrical characteristics may be generated because the first interface comprises a first material and the second interface comprises a second material that is different from the first material.

The first material may comprise a silver substrate that is coated with silver chloride and the second material may comprise gold.

The first interface and the second interface may be formed of the same material and the different electrical characteristics may be generated because the second interface includes an insulation layer between the interface and the skin of an examinee's body.

In another aspect, there is provided a device for use in detecting a biological signal, the device including a first electrode having a first electrical characteristic, a second electrode spaced apart from the first electrode by a first distance and having a second electrical characteristic different from the first electrical characteristic, a third electrode having a third electrical characteristic and spaced apart from the first electrode by a second distance that is greater than the first distance, and a fourth electrode having a fourth electrical characteristic different form the third electrical characteristic and spaced apart from the third electrode by a third distance that is less than the second distance.

The first distance and the third distance may be substantially equal.

The first electrical characteristic and the third electrical characteristic may be substantially the same.

The second electrical characteristic and the fourth electrical characteristic may be substantially the same.

The first electrode may include a first metal and the second electrode may includes a second metal that is different from the first metal.

The first electrode further may include a coating on the first metal.

The first metal may be silver (Ag) and the coating may be silver chloride (AgCl).

The second metal may be gold (Au).

The first and second electrodes may include a metal.

The second electrode further may include an insulation material.

The first and second electrodes may include a coating on the metal.

The metal is silver (Ag) and the coating may be silver chloride (AgCl).

The insulation material may be rubber.

The first, second, third, and fourth electrodes may form a unit and the device may include two or more of the units.

The first, second, third, and fourth electrodes may be arranged in a straight pattern.

The first, second, third, and fourth electrodes may be arranged in a curved pattern.

The curved pattern may be a circular pattern.

In another aspect, there is provided a biological signal measuring apparatus including at least one interface for detecting a biological signal of an examinee through electrical interfacing with a skin of the examinee, at least one dummy interface for detecting a dummy signal that is different from the biological signal, through the at least one dummy interface that has electrical characteristics that are different from those of the at least one interface, and a electronic circuit for removing a noise generated due to a fluctuation in the electrical characteristics of the at least one interface from the detected biological signal, based on the biological signal and the dummy signal.

Other features and aspects may be apparent from the following detailed description, the drawings, and the claims.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

In various examples, to help an examiner such as a doctor in recognizing a biological signal of an examinee, a display or a sheet of paper may be added in addition to the configurations for measuring a biological signal of an examinee.

Figure 1:
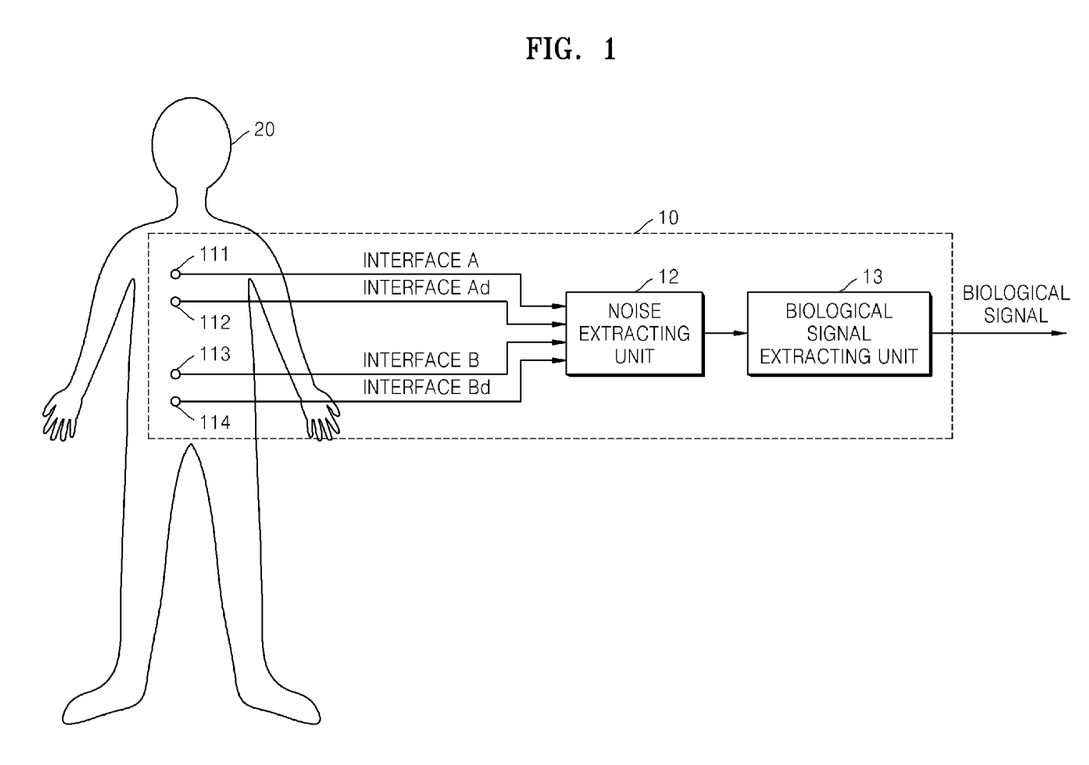
FIG. 1 is a diagram illustrating an example of a biological signal measuring apparatus.

FIG. 1 illustrates an example of a biological signal measuring apparatus.

Referring to FIG. 1, the biological signal measuring apparatus 10 includes interface A 111, interface Ad 112, interface B 113, interface Bd 114, a noise extracting unit 12, and a biological signal extracting unit 13. The biological signal measuring apparatus 10 illustrated in FIG. 1 is an example and may be modified in various ways based on the elements illustrated in FIG. 1. For example, while four interfaces A, Ad, B, and Bd 111 through 114 are illustrated in FIG. 1, the biological signal measuring apparatus 10 may include various numbers of interfaces.

Interfaces A 111 and B 113 may detect a biological signal of an examinee 20 through electrical interfacing with the examinee 20 by touching the skin of the examinee 20. As an example, a biological signal of the examinee 20 may be measured based on the theory that there are different potentials between different parts of the skin of the examinee 20. For example, a biological signal of the examinee 20 may be measured by a potential difference (i.e. voltage) between a pair of interfaces such as interfaces A 111 and B 113. It should also be understood that a biological signal of the examinee 20 may be measured via a potential at one part of the skin of the examinee 20 or a combination of values may be detected via a plurality of interfaces at a plurality of parts of the skin of the examinee 20.

While the interfaces A 111 and B 113, and Ad 112 and Bd 114 are shown as being electrically connected to the noise extracting unit 12, it should also be appreciated that one or more of the interfaces 111 through 114 may wirelessly transmit the result of measuring the biological signal to the noise extracting unit 12. For wireless communication between the interfaces 111 through 114 and the noise extracting unit 12, the interfaces 111 through 114 and the noise extracting unit 12 may include units performing the wireless communication. In this case, the interfaces 111 through 114 can be a separate device from the noise extracting unit 12.

Figure 2:
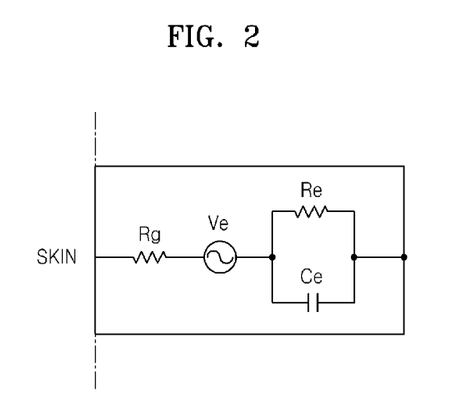
FIG. 2 is a diagram illustrating an example of an equivalent circuit of the interfaces illustrated in FIG. 1.

FIG. 2 illustrates an example of an equivalent circuit of the interfaces illustrated in FIG. 1.

Referring to FIGS. 1-2, the interfaces A 111 and B 113 denote elements that directly touch the skin of the examinee 20 to conduct electrical interfacing with the skin of the examinee 20 to measure a biological signal of the examinee 20. The interfaces A 111 and B 113 may be modeled as resistor-capacitor (RC) circuits as illustrated in FIG. 2.

For example, interfaces A 111 and B 113 may be wet-type electrodes that are formed of a solid conductive material and coated with an electrolyte-containing gel. In this example, the electrodes may contact the skin of the examinee 20 via the gel. As another example, interfaces A 111 and B 113 may be dry-type electrodes that are formed of a solid conductive material and that directly touch the skin of the examinee 20. The skin of the examinee 20 is typically an excellent nonconductor that protects a living body from an external electrical impulse. To mitigate resistance of the skin of the examinee 20, the wet-type electrodes including solid type electrodes may be coated with a substance such as an electrolyte-containing gel including chlorine, a biological ion, and the like. Hereinafter, an example of interfaces A 111 and B 113 being formed using a wet-type electrode is described with reference to the equivalent circuit of FIG. 2.

Referring to FIG. 2, an interface may include a resistor Rg, a voltage source Ve, a capacitor Ce, and a resistor Re. The resistor Rg denotes resistance of an electrolyte of a wet-type electrode, the voltage source Ve denotes a potential that is applied between two ends of the electrode, the capacitor Ce denotes the capacitance in a charge double layer on a boundary surface between the electrode and the electrolyte, and the resistor Re denotes leakage resistance that occurs in the charge double layer.

In various aspects, a charge double layer may be formed on the boundary surface between the electrode and the electrolyte, and motion of the electrode may vary charge distribution on the boundary surface between the electrode and the electrolyte. The variation of the motion of the electrode may vary a potential detected by the electrode. The interfaces A 111 and B 113 may move in different manners. Accordingly, potentials that are detected using the electrodes of the interfaces A 111 and B 113 may vary in different manners from each other, and this variation may create a fluctuation (i.e. noise) in a voltage between the interfaces A 111 and B 113. The noise generated by the fluctuation in the electrical characteristics of the interfaces A and B 111 and 113 is referred to as a motion artifact of a biological signal that is detected using the interfaces A 111 and B 113. A motion artifact may be generated for various factors other than as described above. As an example, if the skin of the examinee 20 is pulled, a motion artifact of 5-10 mV may be generated. This motion artifact may create noise in the biological signal detected from an examinee that is wearing the interfaces.

A motion artifact signal as described above may be a low frequency signal of a frequency band that is similar to that of a biological signal that is detected by the interfaces A 111 and B 113. Accordingly, it may be difficult to remove the noise generated by the motion artifact using a general low pass or high pass filter. As illustrated in FIG. 1, to remove a motion artifact that may be generated as described above, dummy interfaces Ad 112 and Bd 114 may be used to detect dummy signals that are different from a biological signal of the examinee 20 detected via the interfaces A 111 and B 113. The dummy interfaces Ad 112 and Bd 114 may detect dummy signals through interfacing with electrical characteristics different from those of the interfacing of the interfaces A 111 and B 113.

To remove a motion artifact of a biological signal of the examinee 20, a motion artifact signal of the biological signal may be traced using dummy signals that are detected by the dummy interfaces Ad 112 and Bd 114. In this example, if the electrical characteristics of the interfaces Ad 112 and Bd 114 vary due to, for example, motion of the examinee 20, variation aspects of dummy signals detected by the interfaces Ad 112 and Bd 114 may be similar to variation aspects of signals detected by the interfaces A 111 and B 113. For example, the interface A 111 and the dummy interface Ad 112 may be disposed within a distance between each other so that an external noise fluctuation factor is almost simultaneously input to both the interface A 111 and the dummy interface Ad 112. As an example, the distance may be 0.5 mm, 0.75 mm, 1 mm, 1.5 mm, 2 mm, and the like. In other words, the distance may be in the range of 0.1~10 mm. The interface B 113 and the dummy interface Bd 114 may also be disposed within a distance so that an external noise fluctuation factor is almost simultaneously input to both the interface B 113 and the dummy interface Bd 114. In contrast, the interface A 111 and the interface B 113 may be spaced apart by a distance for detecting a biological signal of the examinee 20.

For example, if the interface A 111 and the dummy interface Ad 112 are attached to the skin of the examinee 20 while near to each other, motions of the electrodes of the interface A 111 and the dummy interface Ad 112 may be approximately the same. As a result, a fluctuation in the electrical characteristics of the interface A 111 due to an external factor such as motion of the examinee 20 may be similar to fluctuation in the electrical characteristics of the dummy interface Ad 112. In this example, a fluctuation of a voltage source of an equivalent circuit of the dummy interface Ad 112 may differ in scale from fluctuation of a voltage source of an equivalent circuit of the interface A 111 but may be proportional thereto. Likewise, fluctuation of a voltage source of an equivalent circuit of the dummy interface Bd 114 may differ in scale from fluctuation of a voltage source of an equivalent circuit of the interface B 113 but may be proportional thereto. The nearer an interface and a dummy interface thereof are to each other, the greater the above-described proportional effect.

The noise extracting unit 12 may use the similarity between the fluctuation in the electrical characteristics of the interface A 111 and the fluctuation in the electrical characteristics of the dummy interface Ad 112, and the similarity between the fluctuation in the electrical characteristics of the interface B 113 and the fluctuation in the electrical characteristics of the dummy interface Bd 114, to extract a noise signal that is proportional to a motion artifact signal of a biological signal of the examinee 20 from among signals detected by the interfaces A 111 and B 113 and the dummy interfaces Ad 112 and Bd 114.

For example, the noise extracting unit 12 may use the similarity between the fluctuation in the voltage of the voltage source of the interface A 111 and the fluctuation in the voltage of the voltage source of the dummy interface Ad 112, and the similarity between the fluctuation in the voltage of the voltage source of the interface B 113 and the fluctuation in the voltage of the voltage source of the dummy interface Bd 114, to extract a noise signal that is proportional to a motion artifact signal of a biological signal of the examinee 20 from among signals detected by the interfaces A 111 and B 113 and the dummy interfaces Ad 112 and Bd 114.

The signals detected via the interfaces A 111, B 113, Ad 112, and Bd114 may be small in size. Accordingly, the signals may be amplified for processing. For example, the noise extracting unit 12 may include an amplifier for amplifying signals detected via the interfaces A 111, B 113, Ad 112, and Bd 114, an analog-to-digital (A/D) converter for converting the amplified, analog signals into digital signals, and a calculator for calculating the digital signals.

The biological signal extracting unit 13 may detect an actual biological signal of the examinee 20 by removing a motion artifact signal from a biological signal that is detected by the interfaces A 111 and B 113 using a noise signal that is extracted by the noise extracting unit 12. For example, the noise signal that is extracted by the noise extracting unit 12 may be proportional to the motion artifact signal, and thus the motion artifact signal of the biological signal may be removed using the noise signal extracted by the noise extracting unit 12. The biological signal extracting unit 13 may include an adaptive filter. The adaptive filter may be a digital filter that is capable of adjusting filter coefficients based on values that are fed back by the adaptive filter. For example, the biological signal extracting unit 13 may adjust filter coefficients based on noise signals that are extracted by the noise extracting unit 12 and filter a biological signal corresponding to a waveform of a voltage between the interfaces A 111 and B 113 using the adjusted filter coefficients to remove a motion artifact signal from the biological signal.

The noise extracting unit 12 and the biological signal extracting unit 13 may be an electronic circuit including the above electronic elements or other electronic elements. Electronic elements may not be classified by the noise extracting unit 12 and the biological signal extracting unit 13, because these mean functional blocks for classifying the above mentioned operations. For example, the noise extracting unit 12 and the biological signal extracting unit 13 may be an electronic circuit, using an adaptive filter, removing a motion artifact signal from a biological signal that is detected by the interfaces A 111 and B 113, based on the signals detected via the interfaces A 111, B 113, Ad 112, and Bd114. In this example, the adaptive filter can perform operations detecting the motion artifact signal and the actual biological signal of the examinee 20.

An example of a biological signal that may be measured using a waveform of a voltage detected between the two interfaces A 111 and B 113 is an electrocardiography (ECG) signal. For example, as the heart of the examinee 20 repeatedly beats, a potential difference between different parts of the skin of the examinee 20 may change. A graph illustrating the electrical activity of the heart as described above is referred to as an ECG signal. As another example, the biological signal measuring apparatus 10 illustrated in FIG. 1 may be applied not only to ECG signals but also to other biological signals that may be electrically detected from the body of the examinee 20, such as brain wave signals, electromyogram signals, and the like.

An ECG signal may be measured based on the characteristic that between the heart of the examinee 20 and different parts of the skin are different potential differences. Generally, an ECG signal may be detected by attaching a pair of electrodes to two parts of the skin of the examinee 20 and measuring a potential difference between the electrodes over a predetermined period of time. The measured potential difference between the two electrodes may be shown as a waveform signal that repeatedly rises and declines over time, and this ECG signal may be displayed and/or recorded as a waveform, for example, on a screen or a sheet of paper.

A pair of electrodes that are attached to two parts of the skin of the examinee 20 is a unit for measuring one ECG signal and the electrodes may be referred to as leads. Generally, an ECG signal is measured using any of various numbers of leads, and the heart of the examinee 20 may be observed at different angles through the leads, respectively. For example, ECG signals may be classified as a 3-lead, a 5-lead, a 12-lead, and the like, based on the number of leads. For convenience, an ECG signal measuring apparatus described herein includes two leads, however, it should be appreciated that the biological signal measuring apparatus 10 may instead or also measure another number of leads, for example, a 3-lead, a 5-lead, or a 12-lead ECG signal.

Figure 3:
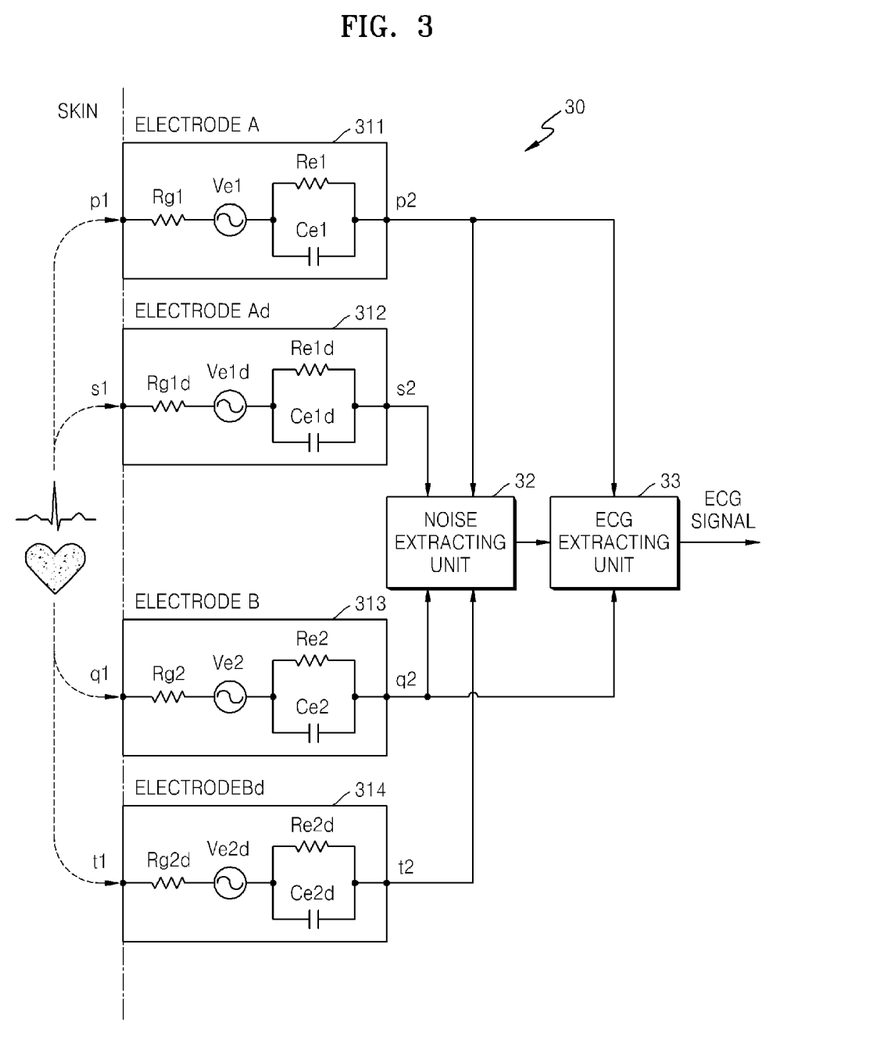
FIG. 3 is a diagram illustrating an example of an electrocardiography signal measuring apparatus.

FIG. 3 illustrates an example of an ECG signal measuring apparatus. The ECG signal measuring apparatus is an example of the biological signal measuring apparatus 10 illustrated in FIG. 1. Thus, descriptions already described with reference to the biological signal measuring apparatus 10 illustrated in FIG. 1 such as descriptions related to the biological signal extracting unit 33, may be omitted here but also apply to the ECG signal measuring apparatus 30 illustrated in FIG. 3.

Referring to FIG. 3, ECG signal measuring apparatus includes an electrode A 311 and an electrode B 313 that are formed by coating a flat substrate formed of silver (Ag) with silver chloride (AgCl) and are referred to as Ag/AgCl electrodes. In the example of FIG. 3, dummy electrodes Ad 312 and Bd 314 are formed of a material that is different from that of the electrodes A 311 and B 313 so that the dummy electrodes Ad 312 and Bd 314 have electrical characteristics that are different from those of the electrodes A 311 and B 313. For example, the dummy electrodes Ad 312 and Bd 314 may be formed of a flat substrate formed of gold (Au).

In this example, a voltage between an output end p2 of the electrode A 311 and an output end q2 of the electrode B 313 may be calculated as shown in Equation 1 below. In Equation 1, Vecg_p1 denotes a potential at an input end p1 of the electrode A 311 and Ve1 denotes a voltage between the input and output ends p1 and p2 of the electrode A 311. Also in Equation 1, Vecg_q1 denotes a potential at an input end q1 of the electrode B 313 and Ve2 denotes a voltage between the input and output ends q1 and q2 of the electrode B 313. For a wet-type electrode, because electrolyte-containing gel is inserted between the skin of the examinee 20 and the electrodes, interfacing between the skin of the examinee 20, the gel, and the electrode may be considered to determine Ve1 and Ve2, and this may also be applied to following Equations.

Referring to Equation 1, Vecg_p1−Vecg_q1 denotes a pure ECG signal, and Vnoise denotes a motion artifact signal that is included in an ECG signal that is detected using the electrode A 311 and the electrode B 313.

$$Vp2\text{-}q2 = (\text{Vecg\_p1} + Ve1) - (\text{Vecg\_q1} + Ve2) \quad [\text{Equation 1}]$$
$$= (\text{Vecg\_p1} - \text{Vecg\_q1}) + (Ve1 - Ve2)$$
$$= Vecg + Vnoise$$

A voltage between the output end p2 of the electrode A 311 and an output end s2 of the dummy electrode Ad 312 may be calculated as shown in Equation 2. In Equation 2, Vecg_s1 denotes a potential at an input end s1 of the dummy electrode Ad 312, and Ve1$d$ denotes a voltage that is between the input and output ends s1 and s2 of the dummy electrode Ad 312. For example, because the electrode A 311 and the dummy electrode Ad 312 are placed near to each other, Vecg_p1 at the input end p1 of the electrode A 311 and Vecg_s1 at the input end s1 of the dummy electrode Ad 312 may be approximately the same. Accordingly, referring to Equation 2, Vp2−s2 may be the same as Ve1−Ve1$d$ because Vecg_p1−Vecg_s1 is considered to be equal to zero.

$$Vp2\text{-}s2 = (\text{Vecg\_p1} + Ve1) - (\text{Vecg\_s1} + Ve1d) \quad [\text{Equation 2}]$$
$$= (\text{Vecg\_p1} - \text{Vecg\_s1}) + (Ve1 - Ve1d)$$
$$= Ve1 - Ve1d$$

A voltage that is between the output end q2 of the electrode B 313 and an output end t2 of the dummy electrode Bd 314 may be calculated as shown in Equation 3. In Equation 3, Vecg_q1 denotes the potential at the input end q1 of the electrode B 313 and Ve2 denotes the voltage between the input and output ends q1 and q2 of the electrode B 313. Also in Equation 3, Vecg_t1 denotes a potential at an input end t1 of the dummy electrode Bd 314 and Ve2$d$ denotes a voltage that is between the input and output ends t1 and t2 of the dummy electrode Bd 314. Because the electrode B 313 and the dummy electrode Bd 314 are placed near to each other, Vecg_q1 at the input end q1 of the electrode B 313 and Vecg_t1 at the input end t1 of the dummy electrode Bd 314 may be approximately the same. Referring to Equation 3, Vq2−t2 may be the same as Ve2−Ve2$d$ because Vecg_q1−Vecg_t1 is considered to be equal to zero.

$$Vq2\text{-}t2 = (\text{Vecg\_q1} + Ve2) - (\text{Vecg\_t1} + Ve2d) \quad [\text{Equation 3}]$$
$$= (\text{Vecg\_q1} - \text{Vecg\_t1}) + (Ve2 - Ve2d)$$
$$= Ve2 - Ve2d$$

In this example, V(p2−s2)−(q2−t2) is a value obtained by subtracting Vq2−t2 of Equation 3 from Vp2−s2 of Equation 2 and may be calculated as shown in Equation 4. In Equation 4, a is a proportional constant. Because the electrode A 311 and the dummy electrode Ad 312 are placed near to each other, a fluctuation of a voltage source of an equivalent circuit of the dummy electrode Ad 312 may be approximately the same as that of a voltage source of an equivalent circuit of the electrode A 311. Accordingly, Ve1$d$ may be equal to b*Ve1. Also, a fluctuation of a voltage source of an equivalent circuit of the dummy electrode Bd 314 may be approximately the same as that of a voltage source of an equivalent circuit of the electrode B 313. Accordingly, Ve2$d$ may be equal to b*Ve2. In this example, b represents a proportional constant, and a=1−b. Referring to Equation 4 below, (V(p2−s2)−(q2−t2)) is proportional to Vnoise included in a detected biological signal.

$$V(p2\text{-}s2) - (q2\text{-}t2) = (Ve1 - Ve1d) - (Ve2 - Ve2d) \quad [\text{Equation 4}]$$
$$= (Ve1 - Ve2) - (Ve1d - Ve2d)$$
$$= a*(Ve1 - Ve2) = a*Vnoise$$

The noise extracting unit 32 may extract a signal that is proportional to a motion artifact signal that is included in an ECG signal detected by the electrode A 311 and the electrode B 313. For example, the noise extracting unit 32 may measure a voltage Vp2−s2 between the output end p2 of the electrode A 311 and the output end s2 of the dummy electrode Ad 312 and may measure a voltage (Vq2−t2) between the output end q2 of the electrode B 313 and the output end t2 of the dummy electrode Bd 314, and calculate the difference between the measured voltages.

In order to place the electrode A 311 and the dummy electrode Ad 312 near enough to each other such that fluctuation aspects of the electrical characteristics of the electrode A 311 and that of the dummy electrode Ad 312 due to external factors become similar, the electrode A 311 and the dummy electrode Ad 312 may be relatively small in size.

Further described herein are various examples in which one electrode and one dummy electrode are divided into a plurality of unit electrodes and a plurality of unit dummy electrodes, respectively. Also described are various examples in which the unit dummy electrodes are alternately arranged between the unit electrodes, such that the electrode A 311 and the dummy electrode Ad 312 are placed near to each other and such that a sufficient amount of current may be measured to accurately measure a biological signal of the examinee 20.

Figure 4:
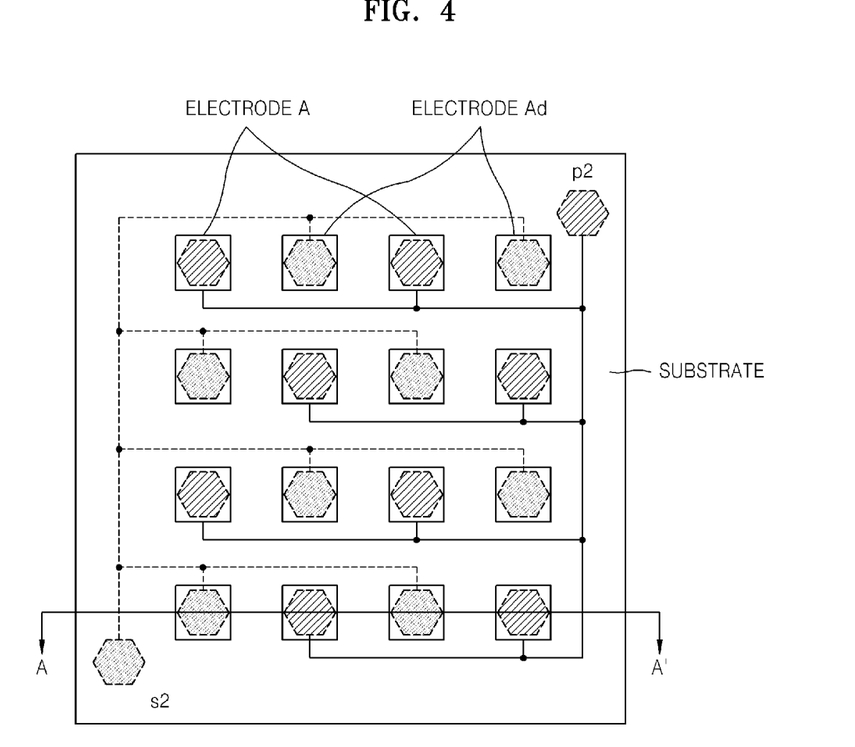
FIG. 4 is a diagram illustrating an example of a latticed electrode substrate of the electrocardiography signal measuring apparatus illustrated in FIG. 3.

FIG. 4 illustrates an example of a latticed electrode substrate of the ECG signal measuring apparatus illustrated in FIG. 3.

FIG. 4 illustrates an arrangement of the electrode A 311 and the dummy electrode Ad 312 of the ECG signal measuring apparatus 30 that are illustrated in FIG. 3. Referring to FIG. 4, a plurality of unit electrodes corresponding to the electrode A 311 are arranged in a lattice structure on a substrate that may be formed of an insulation material, and a plurality of unit dummy electrodes corresponding to the dummy electrode Ad 312 are arranged between the unit electrodes in a lattice structure. The unit electrodes arranged in a lattice structure are connected to a node p2 that corresponds to an output end of the electrode A 311. Accordingly, current detected through the unit electrodes is collected by the node p2. Likewise, the unit dummy electrodes arranged in a lattice structure are connected to a node s2 that corresponds to an output end of the dummy electrode Ad 312. Accordingly, current detected through the unit dummy electrodes is collected by the node s2. Using the lattice structure arrangement, the electrode A 311 and the dummy electrode Ad 312 may be placed near to each other, and a sufficient amount of current for accurately measuring a biological signal of the examinee 20 may be detected.

Figure 5:
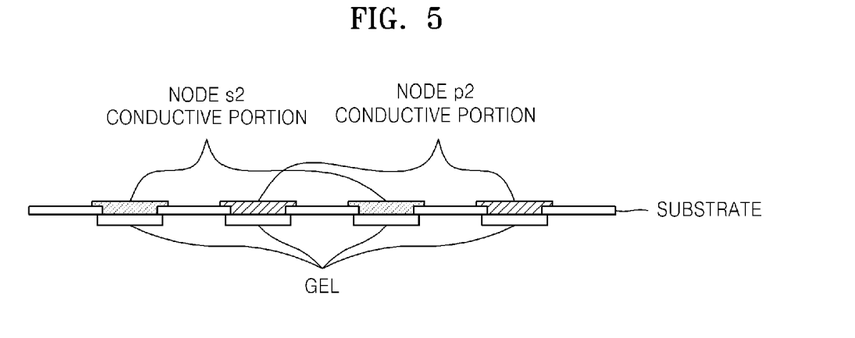
FIG. 5 is a diagram illustrating an example of a cross-sectional view of the latticed electrode substrate of the electrocardiography signal measuring apparatus illustrated in FIG. 4.

FIG. 5 illustrates an example of a cross-sectional view of the latticed electrode substrate of the ECG signal measuring apparatus 30 illustrated in FIG. 4.

Referring to FIG. 5, the electrode substrate of FIG. 4 is cut along a line AA'. In FIG. 5, conductive portions denoted by solid oblique lines correspond to a conductor portion of the unit electrodes that are connected to the node p2, and conductive portions denoted by dotted oblique lines correspond to a conductor portion of the unit dummy electrodes that are connected to the node s2. An electrolyte-containing gel may be adhered to surfaces of each of the unit electrodes and the unit dummy electrodes.

Figure 6:
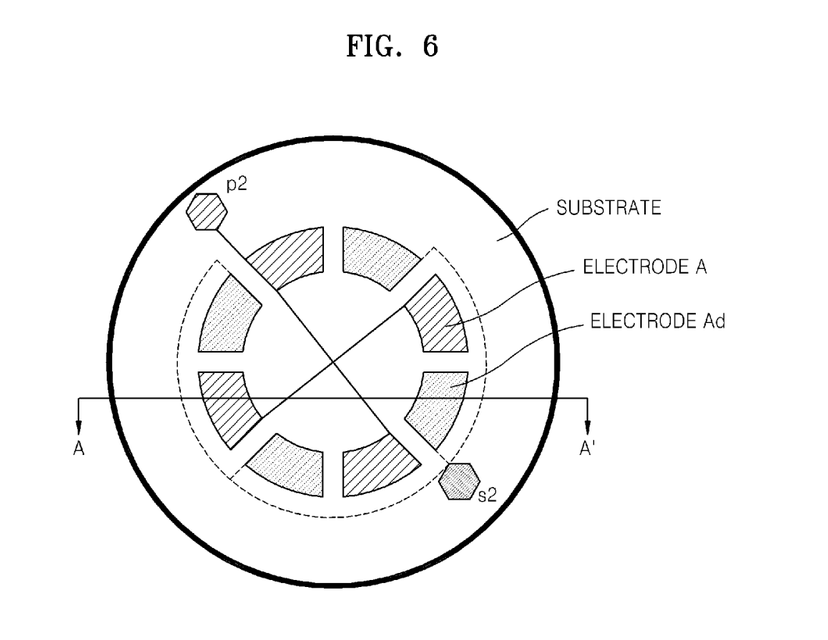
FIG. 6 is a diagram illustrating an example of a circular electrode substrate of the electrocardiography signal measuring apparatus illustrated in FIG. 3.

FIG. 6 illustrates an example of a circular electrode substrate of the ECG signal measuring apparatus 30 illustrated in FIG. 3. FIG. 6 shows an arrangement of the electrode A 311 and the dummy electrode Ad 312 that is another example of that shown in FIG. 3.

Referring to FIG. 6, a plurality of unit electrodes corresponding to the electrode A 311 are arranged in a circular structure on a substrate that may be formed of an insulation material, and a plurality of unit dummy electrodes corresponding to the dummy electrode Ad 312 are arranged between the unit electrodes in a circular structure. The unit electrodes arranged in a circular structure are connected to the node p2 that corresponds to an output end of the electrode A 311. Accordingly, current detected through the unit electrodes may be collected by the node p2. Likewise, the unit dummy electrodes arranged in a circular structure are connected to the node s2 that corresponds to an output end of the dummy electrode Ad 312. Accordingly, current detected through the unit dummy electrodes may be collected by the node s2. In the circular structure, the electrode A 311 and the dummy electrode Ad 312 may be placed near to each other, and a sufficient amount of current for accurately measuring a biological signal of the examinee 20 may be detected.

Figure 7:
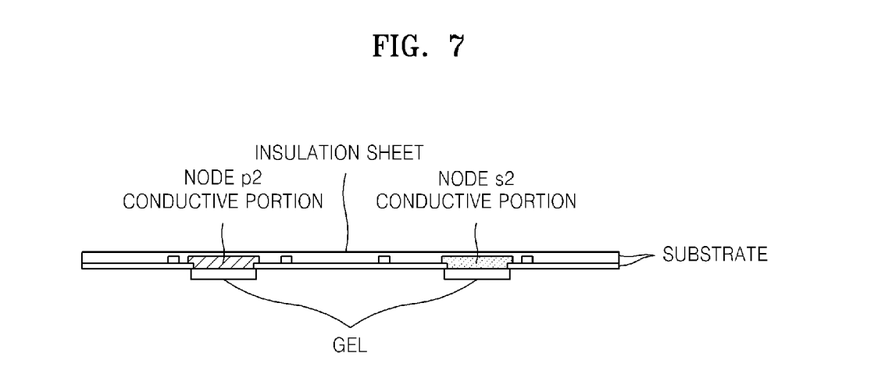
FIG. 7 is a diagram illustrating an example of a cross-sectional view of the circular electrode substrate of the electrocardiography signal measuring apparatus illustrated in FIG. 6.

FIG. 7 illustrates an example of a cross-sectional view of the circular electrode substrate of the ECG signal measuring apparatus illustrated in FIG. 6.

Referring to FIG. 7, the electrode substrate of FIG. 6 is cut along a line AA'. In FIG. 7, conductive portions denoted by solid oblique lines correspond to conductor portions of the unit electrodes that are connected to the node p2, and conductive portions denoted by dotted oblique lines correspond to conductor portions of the unit dummy electrodes that are connected to the node s2. An electrolyte-containing gel may be adhered to the surfaces of each of the unit electrodes and the unit dummy electrodes. As illustrated in FIG. 7, an insulation sheet may be formed on the substrate on which the unit electrodes and the unit dummy electrodes are arranged. In this example, the use of the insulation sheet may block an external current from being supplied to the electrodes, and a more accurate measurement of a biological signal of the examinee 20 may be obtained.

Figure 8:
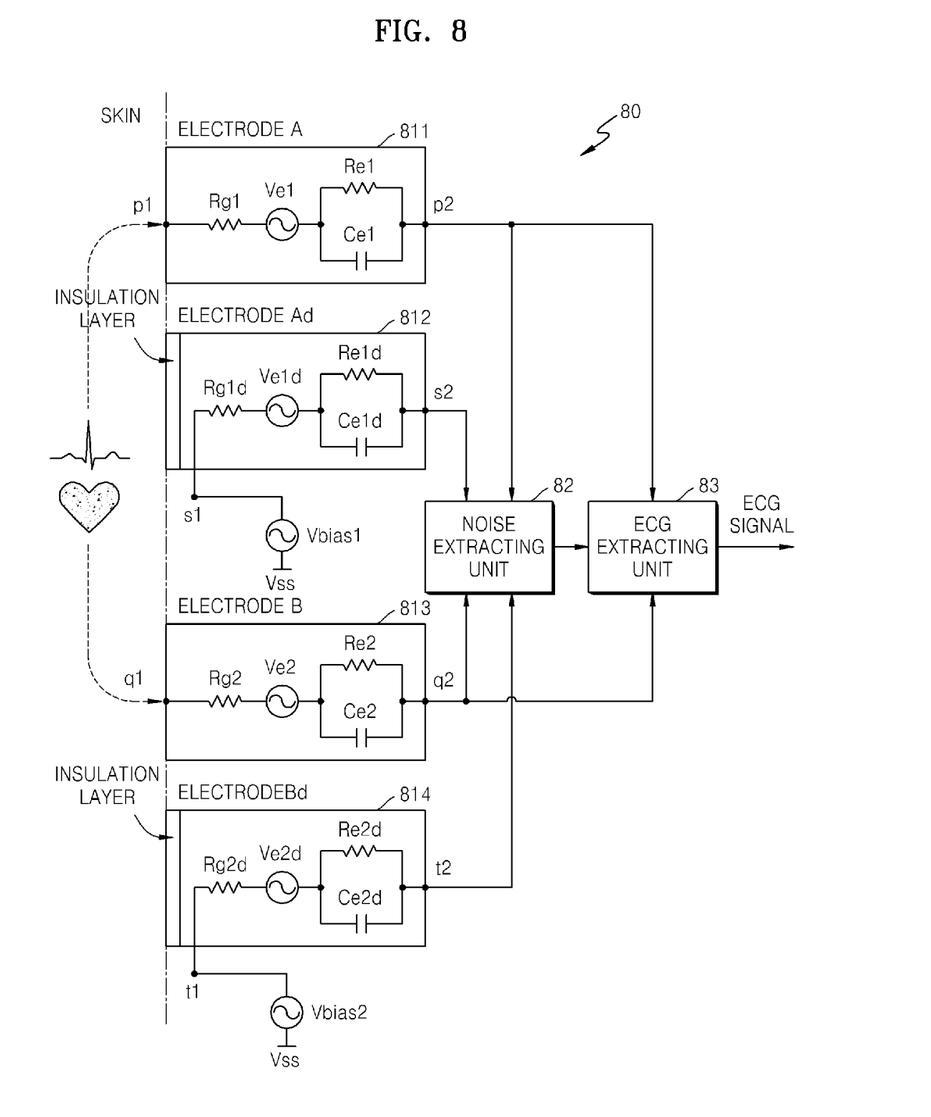
FIG. 8 is diagram illustrating another example of an electrocardiography signal measuring apparatus.

FIG. 8 illustrates another example of an ECG signal measuring apparatus. The ECG signal measuring apparatus 80 illustrated in FIG. 8 is another example of the biological signal measuring apparatus 10 that is illustrated in FIG. 1. Thus, descriptions already described with reference to the biological signal measuring apparatus 10 illustrated in FIG. 1, such as descriptions related to the noise extracting unit 82 and the biological signal extracting unit 83, may be omitted here but also apply to the ECG signal measuring apparatus 80 illustrated in FIG. 8.

In this example, an electrode A 811 and a dummy electrode Ad 812 are formed of the same material, for example, Ag/AgCl. An electrode B 813 and a dummy electrode Bd 814 are also formed of the same material. According to the example of FIG. 8, in order for the dummy electrodes Ad 812 and Bd 814 to have electrical characteristics that are different from those of the electrodes A 811 and B 813, insulation layers may be formed in the dummy electrodes Ad 812 and Bd 814, at portions that touch the skin of the examinee 20 so as to block current that flows from the skin of the examinee 20 to the dummy electrodes Ad 812 and Bd 814. For example, input ends of the dummy electrodes Ad 812 and Bd 814 touching the skin of the examinee 20 may be coated with an insulation material such as rubber. By including the insulation layers in the dummy electrodes Ad 812 and Bd 814, a current from the skin of the examinee 20 may be prevented from affecting the dummy electrodes Ad 812 and Bd 814. In the example of FIG. 8, external bias voltage sources are connected to the input ends of the dummy electrode 812 to apply predetermined voltages to the dummy electrodes Ad 812 and Bd 814.

For example, a voltage between an output end p2 of electrode A 811 and an output end q2 of the electrode B 813 may be calculated as shown in Equation 5 below. In this example, $Vecg\_p1$ denotes a potential at an input end p1 of the electrode A 811 and Ve1 denotes a voltage between the input and output ends p1 and p2 of the electrode A 811. Likewise, $Vecg\_q1$ denotes a potential at an input end q1 of the electrode B 813 and Ve2 denotes a voltage between the input and output ends q1 and q2 of the electrode B 813. Referring to Equation 5, $Vecg\_p1 - Vecg\_q1$ is a pure ECG signal, and Vnoise denotes a motion artifact signal that is included in a ECG signal that is detected by the electrode A 811 and the electrode B 813.

$$Vp2\text{-}q2 = (Vecg\_p1 + Ve1) - (Vecg\_q1 + Ve2) \quad \text{[Equation 5]}$$
$$= (Vecg\_p1 - Vecg\_q1) + (Ve1 - Ve2)$$
$$= Vecg + Vnoise$$

A voltage between an output end s2 of the dummy electrode Ad 812 corresponding to electrode A 811 and an output end t2 of the dummy electrode Bd 814 corresponding to electrode B 813 may be calculated as shown in Equation 6 below. In Equation 6, Vbias1 denotes a potential at an input end s1 of the dummy electrode Ad 812 and Ve1$d$ denotes a voltage between the input and output ends s1 and s2 of the dummy electrode Ad 812. Likewise, Vbias2 denotes a potential at an input end t1 of the dummy electrode Bd 814 and Ve2$d$ denotes a voltage between the input and output ends t1 and t2 of the dummy electrode Bd 814. Vbias1 and Vbias2 correspond to a potential of an external bias voltage source. In this example, the potentials of the external bias voltage sources respectively connected to the dummy electrodes Ad and Bd 812 and 814 may be adjusted as desired. When Vbias1 and Vbias2 are set to be the same, Vs2−t2=Ve1$d$−Ve2$d$.

Because the electrode A 811 and the dummy electrode Ad 812 are placed near to each other, fluctuation of a voltage source of an equivalent circuit of the dummy electrode Ad 812 may be approximately the same as that of a voltage source of an equivalent circuit of the electrode A 811. Accordingly, Ve1$d$=b*Ve1. Likewise, fluctuation of a voltage source of an equivalent circuit of the dummy electrode Bd 814 may be approximately the same as that of the voltage source of an equivalent circuit of the electrode B 813. Accordingly, Ve2$d$=b*Ve2. In these examples, b represents a proportional constant. Referring to Equation 6 below, (Vs2−t2) is proportional to Vnoise that corresponds to a motion artifact signal that is included in an ECG signal detected using the electrode A 811 and the electrode B 813.

$$Vs2\text{-}t2 = (Vbias1 + Ve1d) - (Vbias2 + Ve2d) \quad \text{[Equation 6]}$$
$$= (Vbias1 - Vbias2) + (Ve1d - Ve2d)$$
$$= Ve1d - Ve2d = b*(Ve1 - Ve2) = b*Vnoise$$

The noise extracting unit 12 measures a voltage between the output end s2 of the dummy electrode Ad 812 and the output end t2 of the dummy electrode Bd 814, thereby extracting a signal proportional to Vnoise. In this example, Vbias1 and Vbias2 are approximately the same.

Figure 9:
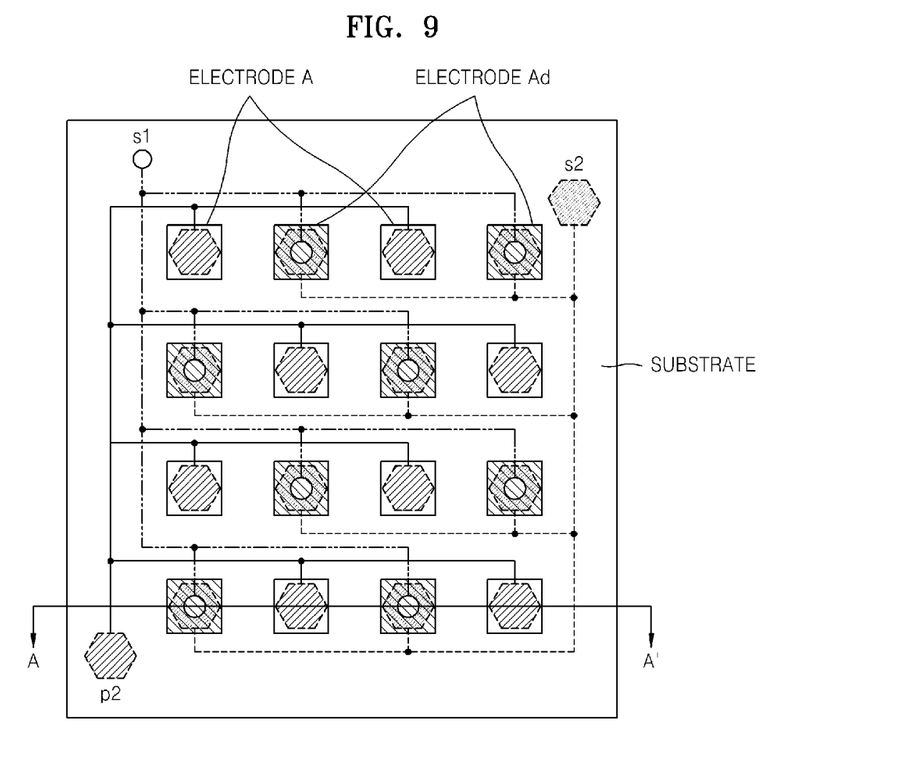
FIG. 9 is a diagram illustrating an example of a latticed electrode substrate of the electrocardiography signal measuring apparatus illustrated in FIG. 8.

FIG. 9 illustrates an example of a latticed electrode substrate of the ECG signal measuring apparatus 80 illustrated in FIG. 8. FIG. 9 illustrates an example of the electrode A 811 and the dummy electrode Ad 812 of the ECG signal measuring apparatus 80 illustrated in FIG. 8. In this example, the latticed electrode substrate of the ECG signal measuring apparatus 80 has the same structure as the latticed electrode substrate illustrated in FIG. 4 except that the insulation layers are formed in the dummy electrodes Ad 812 and Bd 814. In this example, node s1 for supplying power of a predetermined voltage to the unit dummy electrodes is included in addition to the nodes p2 and s2 illustrated in FIG. 4.

Figure 10:
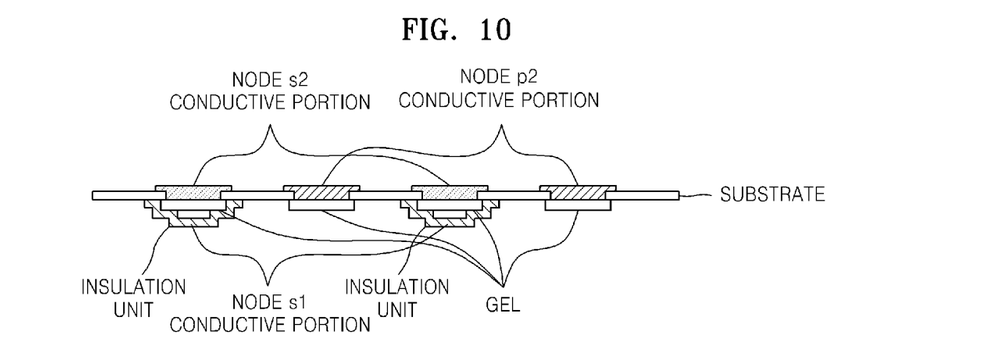
FIG. 10 is a diagram illustrating an example of cross-sectional view of the latticed electrode substrate of the electrocardiography signal measuring apparatus illustrated in FIG. 9.

FIG. 10 illustrates an example of a cross-sectional view of the latticed electrode substrate of the ECG signal measuring apparatus illustrated in FIG. 9. In FIG. 10, the electrode substrate of FIG. 9 is cut along a line AA'. In FIG. 10, conductive portions denoted by solid oblique lines correspond to conductor portions of the unit electrodes that are connected to the node p2, and conductive portions denoted by dotted oblique lines correspond to conductor portions of the unit dummy electrodes that are connected to the node s2. In this example, an electrolyte-containing gel is adhered to the surfaces of each of the unit electrodes and the unit dummy electrodes. Unlike the latticed electrode substrate illustrated in FIG. 5, the unit dummy electrodes include an insulation unit.

Figure 11:
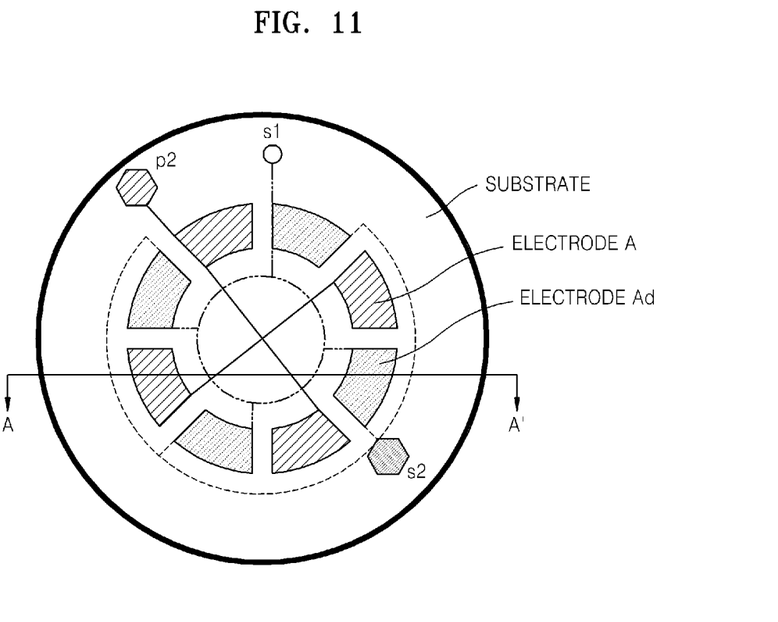
FIG. 11 is a diagram illustrating an example of a circular electrode substrate of the electrocardiography signal measuring apparatus illustrated in FIG. 8.

FIG. 11 illustrates an example of a circular electrode substrate of the ECG signal measuring apparatus 80 illustrated in FIG. 8. FIG. 11 illustrates another example of the electrode A 811 and the dummy electrode Ad 812 illustrated in FIG. 8. In this example, the circular electrode substrate of FIG. 11 has the same structure as the circular electrode substrate illustrated in FIG. 6 except that the insulation layers are formed in the dummy electrodes Ad 812 and Bd 814. In this example, node s1 for supplying power of a predetermined voltage to the unit dummy electrodes is included in addition to the nodes p2 and s2 illustrated in FIG. 6.

Figure 12:
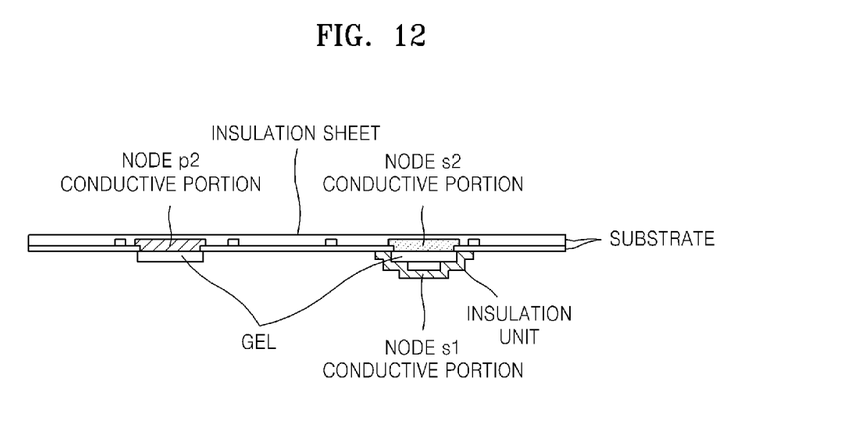
FIG. 12 is a diagram illustrating an example of a cross-sectional view of the circular electrode substrate of the electrocardiography signal measuring apparatus illustrated in FIG. 11.

FIG. 12 illustrates an example of a cross-sectional view of the circular electrode substrate of the ECG signal measuring apparatus illustrated in FIG. 11. In FIG. 12, the electrode substrate of FIG. 11 is cut along a line AA'. In FIG. 12, conductive portions denoted by solid oblique lines correspond to conductor portions of the unit electrodes that are connected to the node p2, and conductive portions denoted by dotted oblique lines corresponds to a conductor portion of the unit dummy electrodes that are connected to the node s2. In this example, an electrolyte-containing gel is adhered to the surfaces of each of the unit electrodes and the unit dummy electrodes. As illustrated in FIG. 12, an insulation sheet may be formed on the substrate on which the unit electrodes and the unit dummy electrodes are arranged. Unlike the latticed electrode substrate illustrated in FIG. 7, in this example the unit dummy electrodes include an insulation unit.

Figure 13:
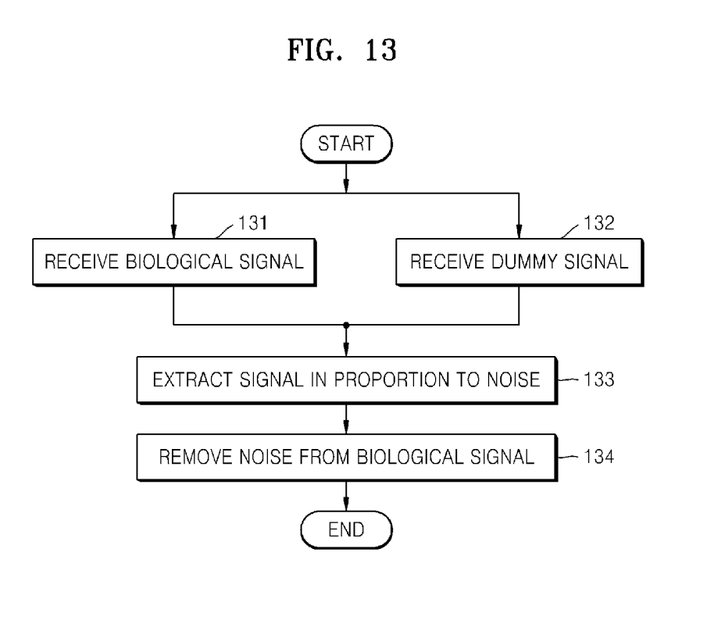
FIG. 13 is a flowchart illustrating an example of a method for measuring a biological signal.

FIG. 13 illustrates an example of a method for measuring a biological signal. The method illustrated in FIG. 13 includes operations that are time-sequentially processed in the biological signal measuring apparatus 10 illustrated in FIG. 1. Accordingly, descriptions already described with reference to the biological signal measuring apparatus 10 illustrated in FIG. 1 may be omitted here but also apply to the method illustrated in FIG. 13.

In 131, the noise extracting unit 12 receives a biological signal of the examinee 20 that is detected via the interfaces A 111 and B 113 that are touching the skin of the examinee 20. In 132, the noise extracting unit 12 receives dummy signals detected via the dummy interfaces Ad 112 and Bd 114 which have electrical characteristics that are different from those of the interfaces A 111 and B 113. In 133, the noise extracting unit 12 extracts a signal that is proportional to noise due to fluctuations in the electrical characteristics of the biological signal of the examinee 20 received in 131 and the dummy signals received in operation 132. In 134, the biological signal extracting unit 13 uses the signal extracted in 133 to remove noise generated due to the fluctuations in the electrical characteristics of the interfaces A 111 and B 113, from the biological signal detected in 131, thereby more accurately detecting a biological signal of the examinee 20.

In various examples described herein, by removing or reducing noise of a biological signal of the examinee 20 generated due to external factors, the biological signal of the examinee 20 may be more accurately measured. For example, by removing or reducing a motion artifact of an ECG signal of the examinee 20 generated due to motion of the examinee 20, the ECG signal of the examinee 20 may be more accurately measured.

Furthermore, as described herein, the noise extracting unit 12 and the biological signal extracting unit 13 illustrated in FIG. 1 may include an amplifier, an A/D converter, a calculator, a digital filter, and the like, and an operation sequence thereof, that is, the method of measuring a biological signal according to the embodiment of FIG. 13 may be written as computer programs and be implemented in general-use digital computers that execute the computer programs using a computer readable recording medium.

The processes, functions, methods, and/or software described herein may be recorded, stored, or fixed in one or more computer-readable storage media that includes program instructions to be implemented by a computer to cause a processor to execute or perform the program instructions. The media may also include, alone or in combination with the program instructions, data files, data structures, and the like. The media and program instructions may be those specially designed and constructed, or they may be of the kind well-known and available to those having skill in the computer software arts. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules that are recorded, stored, or fixed in one or more computer-readable storage media, in order to perform the operations and methods described above, or vice versa. In addition, a computer-readable storage medium may be distributed among computer systems connected through a network and computer-readable codes or program instructions may be stored and executed in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A biological signal measuring apparatus comprising:
an interface configured to detect a biological signal of an examinee through electrical interfacing with a skin of the examinee;
a dummy interface, having electrical characteristics that are different from electrical characteristics of the interface, configured to detect a dummy signal that is different from the biological signal;
a noise calculating unit configured to calculate a signal that is proportional to noise generated in the biological signal using a similarity between fluctuations in the electrical characteristics of the interface and the dummy interface; and
a biological signal extracting unit configured to remove the noise from the detected biological signal using the calculated signal,
wherein the dummy interface comprises at least one dummy electrode and the interface comerises at least one interface electrode and the at east one dumm electrode is formed of a material that is different from a material of the at least one interface electrode so that the electrical characteristics of the dummy interface are different from the electrical characteristics of the interface.

2. The biological signal measuring apparatus of claim 1, wherein the interface and the dummy interface are placed within a predetermined distance from each other.

3. The biological signal measuring apparatus of claim 2, wherein the interface comprises a plurality of unit interface electrodes that are arranged on a substrate, and the dummy interface comprises a plurality of unit dummy electrodes configured between the unit interface electrodes to enable the interface and the dummy interface to be placed near to each other.

4. The biological signal measuring apparatus of claim 2, wherein the similarity between fluctuations in the electrical characteristics of the interface and the dummy interface is due to the interface and the dummy interface being placed near to each other.

5. The biological signal measuring apparatus of claim 1, wherein:
the at least one interface electrode comprises a first interface electrode and a second interface electrode;
the at least one dummy electrode comprises a first dummy electrode and a second dummy electrode; and
the noise calculating unit calculates a signal that is proportional to the noise by measuring a voltage between the first interface electrode and the first dummy electrode, measuring a voltage between the second interface electrode and the second dummy electrode, and calculating a difference in the measured voltages.

6. The biological signal measuring apparatus of claim 1, wherein the dummy interface has electrical characteristics that are different from those of the interface because the dummy interface has formed therein an insulation layer that is located at a portion of the dummy interface that is adapted to touch the skin of the examinee to reduce current from flowing from the skin of the examinee to the dummy interface.

7. The biological signal measuring apparatus of claim 6, wherein the interface comprises a first interface electrode and a second interface electrode,
the dummy interface comprises a first dummy electrode and a second dummy electrode,
the noise calculating unit calculates a signal that is proportional to the noise by measuring a voltage between the first dummy electrode and the second dummy electrode, and
potentials of voltage sources of the first dummy electrode and the second dummy electrode are approximately the same.

8. The biological signal measuring apparatus of claim 1, wherein the biological signal is an electrocardiography signal of the examinee, and the noise is a motion artifact that is generated by fluctuation in the electrical characteristics of the interface due to an external factor caused by motion of the examinee.

9. A biological signal measuring apparatus comprising:
an interface for detecting a biological signal of an examinee through electrical interfacing with a skin of the examinee;
a dummy interface, having electrical characteristics that are different from electrical characteristics of the interface, for detecting a dummy signal that is different from the biological signal; and an electronic circuit for removing a noise generated in the biological signal using a similarity between fluctuations in the electrical characteristics of the interface and the dummy interface, wherein the dummy interface comprises at least one dummy electrode and the interface comprises at least one interface electrode and the at east one dumm electrode is formed of a material that is different from a material of the at least one interface electrode so that the electrical characteristics of the dummy interface are different from the electrical characteristics of the interface.

* * * * *